United States Patent
Yokoi

(10) Patent No.: US 11,096,641 B2
(45) Date of Patent: Aug. 24, 2021

(54) RADIATION IMAGING APPARATUS AND CALIBRATION METHOD FOR PHOTON COUNTING DETECTOR

(71) Applicant: Hitachi, Ltd., Tokyo (JP)

(72) Inventor: Kazuma Yokoi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/891,831

(22) Filed: Jun. 3, 2020

(65) Prior Publication Data

US 2021/0212646 A1   Jul. 15, 2021

(30) Foreign Application Priority Data

Jan. 10, 2020   (JP) ............................. JP2020-002682

(51) Int. Cl.
*A61B 6/00*   (2006.01)
*H04N 5/32*   (2006.01)
*G01T 1/24*   (2006.01)

(52) U.S. Cl.
CPC ............. *A61B 6/482* (2013.01); *G01T 1/247* (2013.01); *H04N 5/32* (2013.01)

(58) Field of Classification Search
CPC ........... A61B 6/482; G01T 1/247; H04N 5/32
See application file for complete search history.

(56) References Cited

U.S. PATENT DOCUMENTS

| | | | | |
|---|---|---|---|---|
| 4,809,172 A | * | 2/1989 | Hopkinson | G06T 11/005 378/4 |
| 5,729,582 A | * | 3/1998 | Ham | G01N 23/20066 378/86 |
| 9,808,216 B2 | | 11/2017 | Schmidt et al. | |
| 2006/0159223 A1 | * | 7/2006 | Wu | A61B 6/032 378/18 |
| 2007/0041490 A1 | * | 2/2007 | Jha | A61B 6/4241 378/8 |
| 2007/0167716 A1 | * | 7/2007 | Kinahan | A61B 6/405 600/407 |
| 2010/0135564 A1 | * | 6/2010 | Thomsen | A61B 6/032 382/131 |
| 2013/0336443 A1 | * | 12/2013 | Gagnon | A61B 6/4233 378/19 |

(Continued)

*Primary Examiner* — Blake C Riddick
(74) *Attorney, Agent, or Firm* — Mattingly & Malur, PC

(57) ABSTRACT

With the aim of providing a radiation imaging apparatus and a calibration method for photon counting detectors, being able to discriminate between soft and adipose tissues with high accuracy, there is disclosed a radiation imaging apparatus equipped with photon counting detectors which output an electric signal corresponding to photon energy which is energy of radiation photons incident thereon, the radiation imaging apparatus including a storage unit which stores relationships between linear attenuation coefficients and the photon energy with regard to multiple materials; a calculation unit which calculates normalized attenuation coefficients which are linear attenuation coefficients normalized by dividing linear attenuation coefficients per unit of photon energy by a linear attenuation coefficient at given photon energy with respect to each material; and a selection unit which selects basal materials which are used in relation to materials to be discriminated which are intended to be discriminated, based on the normalized attenuation coefficients.

8 Claims, 8 Drawing Sheets

(56) References Cited

U.S. PATENT DOCUMENTS

| | | | | |
|---|---|---|---|---|
| 2014/0233694 | A1* | 8/2014 | Wang | A61B 6/582 |
| | | | | 378/5 |
| 2015/0178957 | A1* | 6/2015 | Zou | G06T 11/006 |
| | | | | 382/131 |
| 2015/0178958 | A1* | 6/2015 | Zou | A61B 6/5205 |
| | | | | 378/19 |
| 2015/0371378 | A1* | 12/2015 | Schmidt | G06K 9/6262 |
| | | | | 378/5 |
| 2018/0214113 | A1* | 8/2018 | Yamakawa | G01N 23/083 |
| 2018/0296171 | A1* | 10/2018 | Shirono | A61B 6/4233 |
| 2019/0086562 | A1* | 3/2019 | Xing | A61B 6/5205 |
| 2019/0251713 | A1* | 8/2019 | Chen | G06N 3/084 |
| 2020/0249179 | A1* | 8/2020 | Yamakawa | A61B 6/00 |

* cited by examiner

RADIATION IMAGING APPARATUS AND CALIBRATION METHOD FOR PHOTON COUNTING DETECTOR

CLAIM OF PRIORITY

The present application claims priority from Japanese Patent Application JP 2020-002682 filed on Jan. 10, 2020, the content of which are hereby incorporated by references into this application.

BACKGROUND OF THE INVENTION

The present invention relates to a radiation imaging apparatus equipped with photon counting detectors, and to a calibration method for photon counting detectors.

BACKGROUND ART

Development of a Photon Counting Computed Tomography (PCCT) apparatus equipped with photon counting detectors which are detectors using a photon counting method is underway. Because the photon counting detectors are capable of measuring photon energy which is energy of radiation photons incident on the detectors, the PCCT apparatus can present a medical image containing more information than conventional CT apparatus, for example, a medical image that discriminates between materials having different compositions. More specifically, a medical image that distinguishes between an iodinated contrast agent which is used for angiography and a calcified plaque in blood vessels is obtained. Additionally, to obtain a medical image that discriminates between materials, it is necessary to calibrate beforehand a relationship between output and photon energy obtained when combinations of multiple basal materials having known compositions and thicknesses are measured by the photon counting detectors on a per detector element basis.

The specification of U.S. Pat. No. 9,808,216 discloses an Artificial Neural Network (AMM) trained using multispectral X-ray projection of basal materials to make it possible to determine information corresponding to compositions of a subject from multispectral X-ray projection of the subject. Also, according to the specification of U.S. Pat. No. 9,808,216, when two basal materials are used, it is desirable to use a material having a low atomic number and a material having a high atomic number, and a combination of Poly-Methyl Meth-Acrylate (PMMA) and aluminum and a combination of polyethylene and Poly-Vinyl Chloride (PVC) are mentioned as examples of use.

SUMMARY OF THE INVENTION

In the specification of U.S. Pat. No. 9,808,216, however, no consideration is taken about discriminating between soft and adipose tissues in muscles among others with high accuracy. Because it is important for diagnosis to evaluate a difference in proportions of fat included in body tissues, it is necessary to discriminate between soft and adipose tissues with high accuracy.

Therefore, the present invention has an object to provide a radiation imaging apparatus and a calibration method for photon counting detectors, being able to discriminate between soft and adipose tissues with high accuracy.

To attain the foregoing object, the present invention resides in a radiation imaging apparatus equipped with photon counting detectors which output an electric signal corresponding to photon energy which is energy of radiation photons incident thereon, the radiation imaging apparatus including: a storage unit which stores relationships between linear attenuation coefficients and the photon energy with regard to multiple materials; a calculation unit which calculates normalized attenuation coefficients which are linear attenuation coefficients normalized by dividing linear attenuation coefficients per unit of photon energy by a linear attenuation coefficient at given photon energy with respect to each material; and a selection unit which selects basal materials which are used in relation to materials to be discriminated which are intended to be discriminated, based on the normalized attenuation coefficients.

Also, the present invention resides in a calibration method for photon counting detectors which output an electric signal corresponding to photon energy which is energy of radiation photons incident thereon, the calibration method including the steps of: obtaining relationships between linear attenuation coefficients and the photon energy with regard to multiple materials; calculating normalized attenuation coefficients which are linear attenuation coefficients normalized by dividing linear attenuation coefficients per unit of photon energy by a linear attenuation coefficient at given photon energy with respect to each material; and selecting basal materials which are used in relation to materials to be discriminated which are intended to be discriminated, based on the normalized attenuation coefficients.

According to the present invention, it is possible to provide a radiation imaging apparatus and a calibration method for photon counting detectors, being able to discriminate between soft and adipose tissues with high accuracy.

DETAILED DESCRIPTION OF THE PREFERRED EMBODIMENTS

In the following, an embodiment of the present invention will be described with reference to the drawings. A radiation imaging apparatus of the present invention is applied to an apparatus equipped with a radiation source and photon counting detectors. The following description refers to an example where a radiation is an X-ray and the radiation imaging apparatus is an X-ray CT apparatus.

First Embodiment

Figure 1:
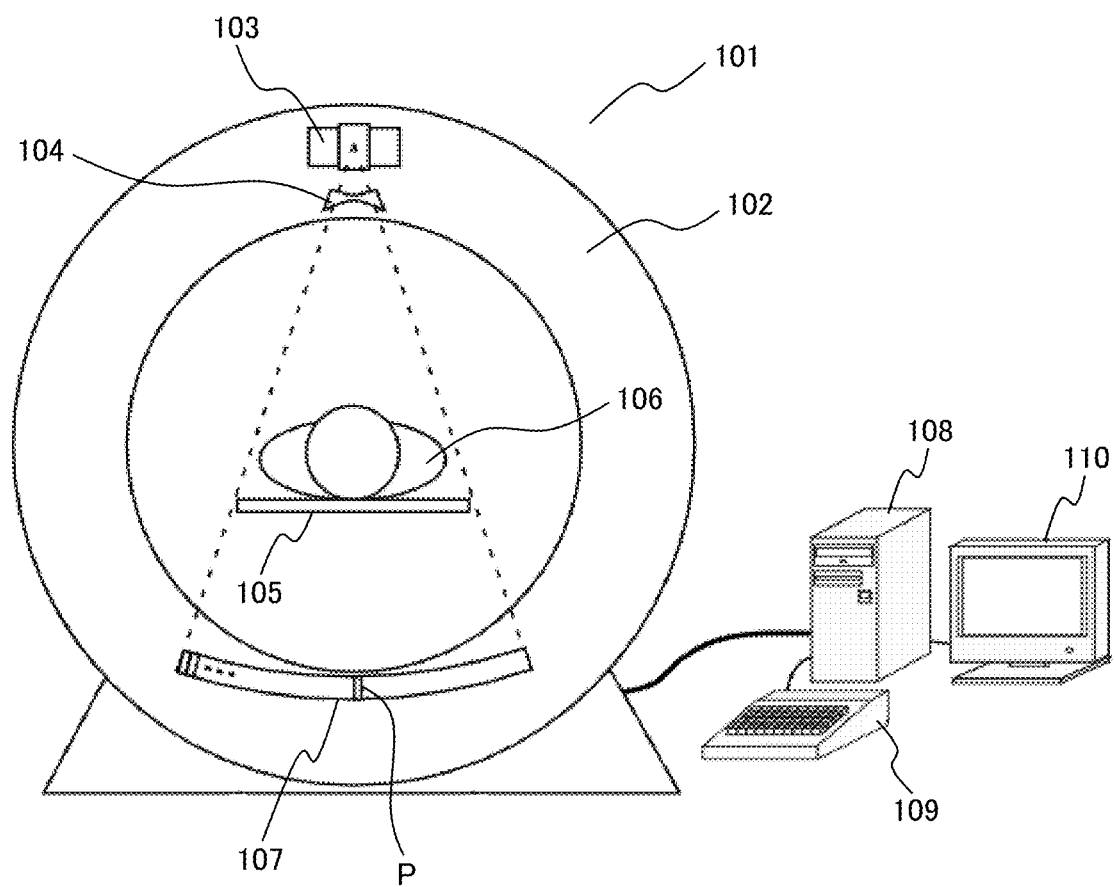
FIG. 1 is a diagram depicting an overall structural of a PCCT apparatus.

FIG. 1 depicts an overall structural diagram of an X-ray CT apparatus 101. The X-ray CT apparatus 101 includes a gantry 102, an X-ray tube 103, a bow-tie filter 104, a bed 105, a detector panel 107, a computational device 108, an input device 109, and a display device 110. X-rays radiated from the X-ray tube 103 are formed in a beam shape suitable for size of a subject 106 by the bow-tie filter 104 and irradiated onto the subject 106, and after penetrating the subject 106, they are detected by the detector panel 107. The X-ray tube 103 and the detector panel 107 are installed to the gantry 102 so as to be placed facing each other across the subject 106 and rotate around the subject 106 by a rotary motion of the gantry 102. By iteration of X-ray irradiation from the X-ray tube 103 and X-ray measurement at the detector panel 107 along with the rotary motion of the gantry 102, projection data at various angles of projection is obtained. Through image reconstruction processing on obtained projection data at the computational device 108, tomographic images of the subject 106 are generated and displayed on the display device 110. In addition, when projection data is obtained while the bed 105 with the subject 106 rested thereon and the gantry 102 move relatively in a direction of the body axis of the subject 106, volume images of the subject 106 are generated. Additionally, X-ray dosage that is irradiated from the X-ray tube 103, the rotating speed of the gantry 102, and the speed of relative movement of the gantry 102 and the bed 105 are set based on scanning conditions that are input by an operator via the input device 109. In addition, the computational device has the same hardware configuration as general computer devices, includes a Central Processing Unit (CPU), a memory, a Hard Disk Drive (HDD), etc., and performs correction processing on projection data among others and control of respective parts.

The detector panel 107 is configured with multiple detector pixels P arranged in an arc shape around the focal point of X rays from the X-ray tube 103. The detector pixels P are photon counting detectors which measure photon energy, i.e., energy of X-ray photons incident thereon, and they produce outputs depending on photon energy.

With the X-ray CT apparatus 101 equipped with the photon counting detectors, a photon energy spectrum regarding projection data of the subject 106 can be obtained and, therefore, it is possible to generate a medical image that discriminates between materials having different compositions and a medical image that classifies these materials into multiple energy components. Additionally, to obtain a medical image that discriminates between materials having different compositions, it is necessary to calibrate beforehand a relationship between output and photon energy obtained when combinations of multiple basal materials having known compositions and thicknesses are measured by the photon counting detectors on a per detector element basis.

Figure 2:
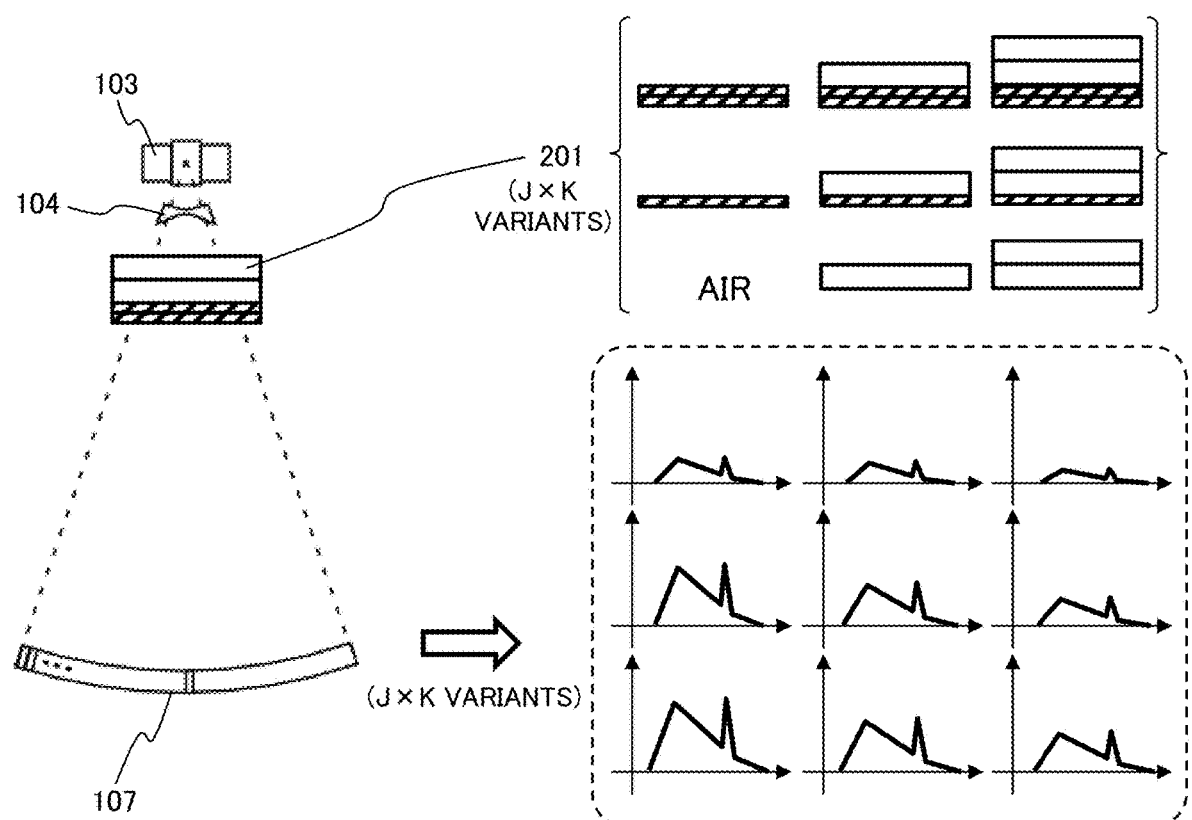
FIG. 2 is a diagram to explain calibration of photon counting detectors.

Calibration of the photon counting detectors is described with FIG. 2. To calibrate the photon counting detectors, as multiple basal materials having known compositions and thicknesses, e.g., combinations 201 of two basal materials are used. As the combinations 201 of basal materials, multiple plates with different thicknesses may be used for each basal material. For example, if plates of one material have J variants of thickness and plates of the other material have K variants of thickness, the combinations 201 of J×K variants of basal materials are used, and photon energy spectra with respect to each combination are obtained. In FIG. 2, because J=3 and K=3, nine variants of photon energy spectra are presented.

To discriminate a desired tissue, e.g., an adipose tissue inside the subject 106 with high accuracy, suitable basal materials must be selected. In the present embodiment, basal materials are selected depending on materials to be discriminated which are intended to be discriminated.

Figure 3:
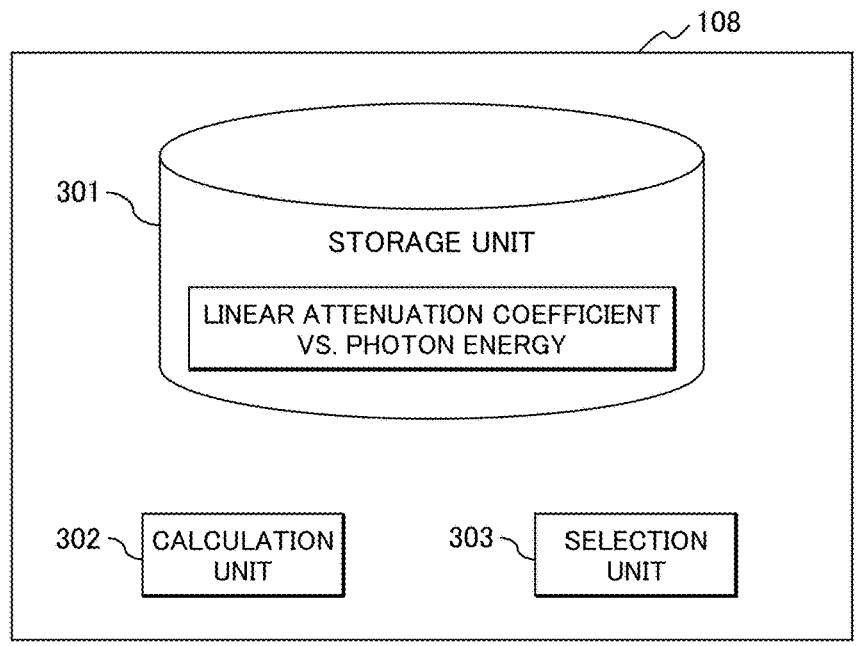
FIG. 3 is a diagram depicting an example of a functional block diagram of an embodiment herein.

An example of a functional block diagram of the present embodiment is described with FIG. 3. Now, these functions may be configured by dedicated hardware structure using Application Specific Integrated Circuits (APSIs), Field Programmable Gate Arrays (FPGAs), etc. or may be configured by software running on the computational device 108. The following description refers to a case where respective functions are configured by software. The present embodiment includes a storage unit 301, a calculation unit 302, and a selection unit 303. Each unit is described below.

Figure 5:
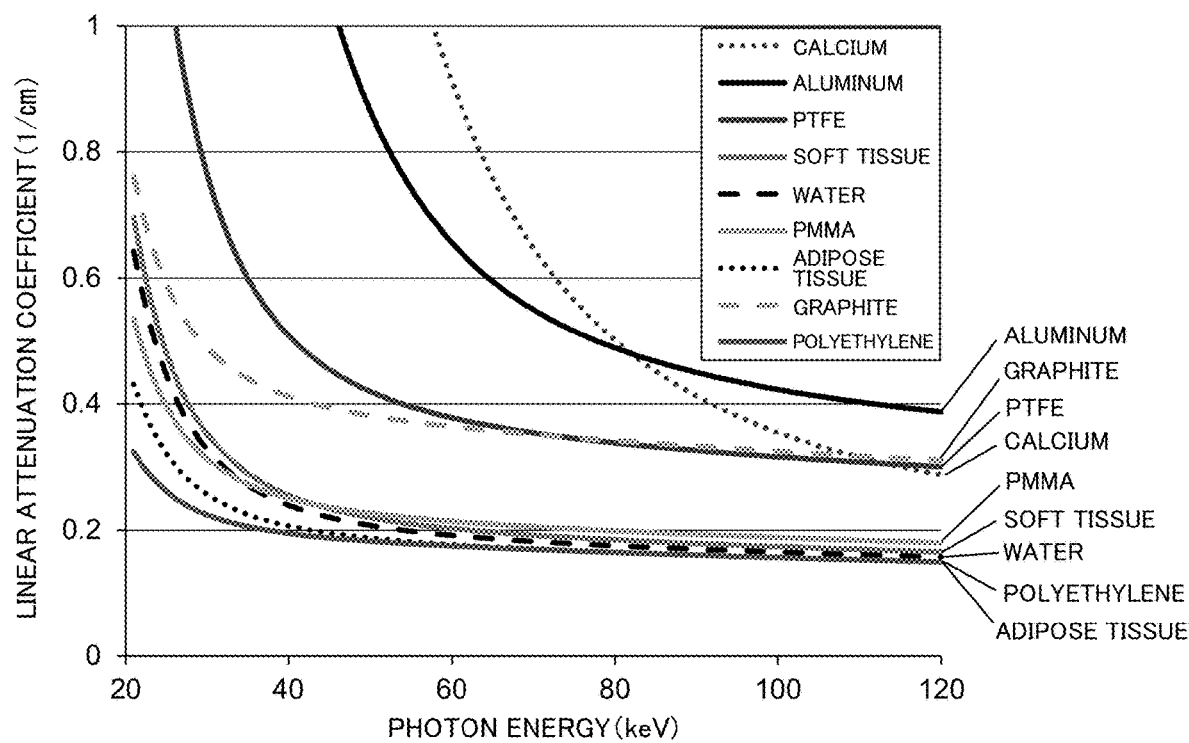
FIG. 5 is a diagram representing an example of relationships between linear attenuation coefficients and photon energy with regard to multiple materials.

The storage unit 301 stores relationships between linear attenuation coefficients of X-rays and photon energy with regard to multiple materials. FIG. 5 represents an example of the relationships between linear attenuation coefficients of X-rays and photon energy. Materials shown in FIG. 5 are calcium, aluminum, Poly-Tetra-Fluoro-Ethylene (PTFE), a soft tissue, water, PMMA, an adipose tissue, graphite, and polyethylene.

Figure 6:
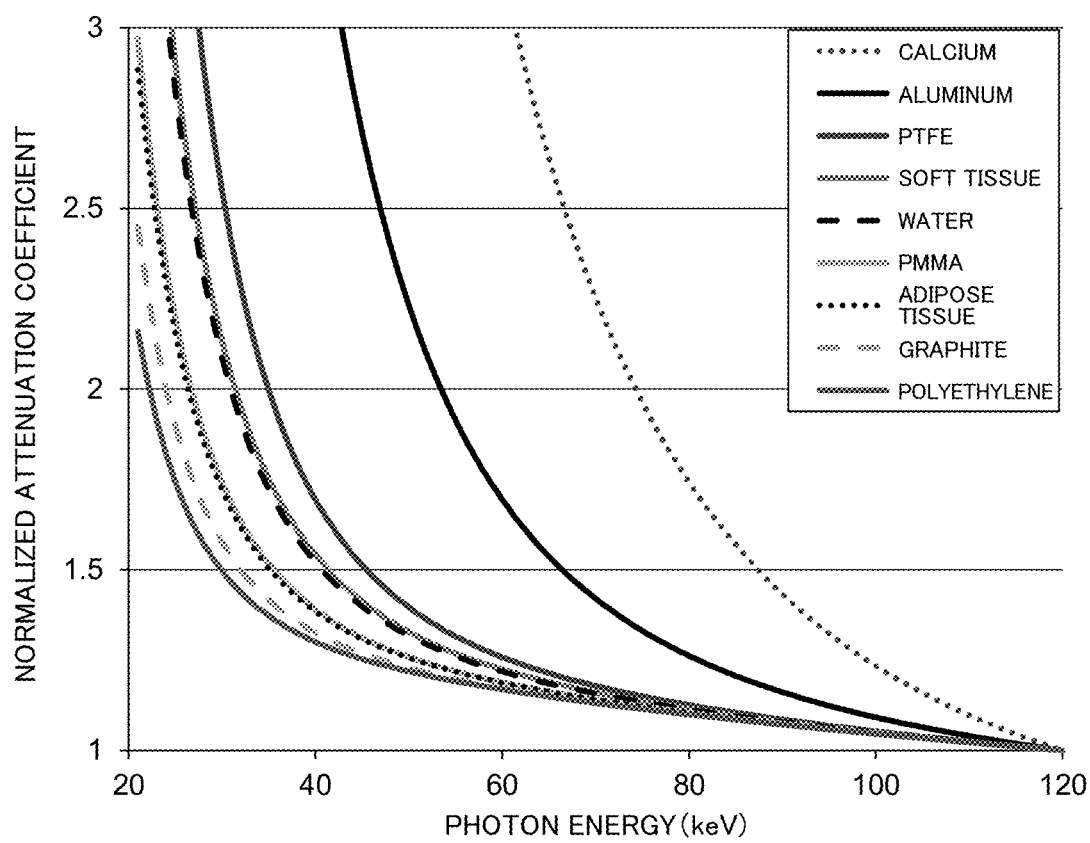
FIG. 6 is a diagram representing an example of relationships between normalized attenuation coefficients and photon energy with regard to multiple materials.

The calculation unit 302 calculates normalized attenuation coefficients which are linear attenuation coefficients normalized by dividing linear attenuation coefficients per unit of photon energy by a linear attenuation coefficient at given photon energy with respect to each material. FIG. 6 represents an example of relationships between normalized attenuation coefficients calculated by dividing linear attenuation coefficients per unit of photon energy by a linear attenuation coefficient at 120 keV and photon energy with respect to each material in FIG. 5.

The selection unit 303 selects basal materials which are used in relation to the materials to be discriminated, based on the normalized attenuation coefficients. More specifically, as the basal materials, a selection is made of a combination of a material having a smaller normalized attenuation coefficient than the normalized attenuation coefficients of the materials to be discriminated and a material having a larger normalized attenuation coefficient than the normalized attenuation coefficients of the materials to be discriminated. Also, as the basal materials, a selection is made of materials having normalized attenuation coefficients with a smaller difference from the normalized attenuation coefficients of the materials to be discriminated. Additionally, because selected basal materials are handled as plates with different thicknesses and measured by the X-ray CT apparatus 101 equipped with the photon counting detectors, it is preferable that they are solids that are stable at ordinary temperature and pressure and that they are materials that are highly homogeneous, easily available, and easy to work.

Figure 4:
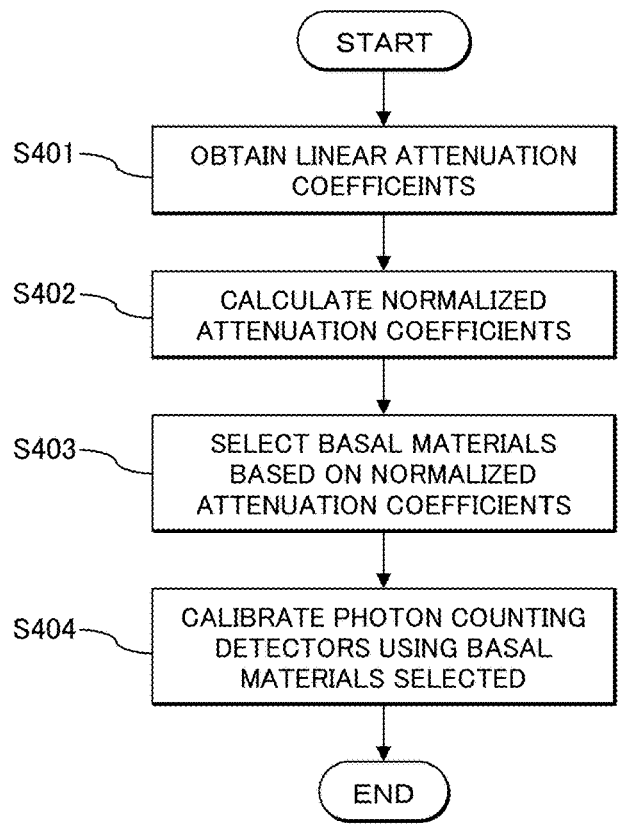
FIG. 4 is a diagram illustrating an example of a processing flow of calibrating the photon counting detectors.

A processing flow of calibrating the photon counting detectors is described with FIG. 4.
(S401)

The calculation unit 302 obtains linear attenuation coefficients regarding multiple materials from the storage unit 301. Additionally, the linear attenuation coefficients are not limited to those that are stored in the storage unit 301 and may be obtained from outside via a network or the like.

As presented in FIG. 5, the linear attenuation coefficients of the respective materials decrease with an increase in photon energy, but a degree of decrease differs depending on the material, and therefore, the curves of the linear attenuation coefficients intersect with each other. This intersection of the curves makes a relationship among the materials unclear and makes it difficult to select basal materials in relation to the materials to be discriminated.

(S402)

The calculation unit 302 calculates normalized attenuation coefficients using the linear attenuation coefficients obtained at S401. Specifically, a normalized attenuation coefficient is calculated by dividing linear attenuation coefficients per unit of photon energy by a linear attenuation coefficient at given photon energy. Additionally, the given photon energy is a photon energy common to all materials, and it is preferable that the given photon energy is maximum energy in a range of photon energy measured by the X-ray CT apparatus 101. For example, when a tube voltage which is applied to the X-ray tube 103 is 120 keV, the linear attenuation coefficients per unit of photon energy are divided by the linear attenuation coefficient at 120 keV.

As presented in FIG. 6, the curves of the normalized attenuation coefficients of the respective materials do not intersect with each other and therefore, the relationship among the materials becomes clear by comparing the normalized attenuation coefficients. That is, by using the normalized attenuation coefficients, it becomes easy to select basal materials in relation to the materials to be discriminated. Additionally, in FIG. 6, order of magnitude of the normalized attenuation coefficients corresponds to order of the materials specified in a legend.

(S403)

The selection unit 303 selects basal materials based on the normalized attenuation coefficients calculated at S402. For example, a first material which is a material in a first material group which is a material group having a smaller normalized attenuation coefficient than the normalized attenuation coefficients of the materials to be discriminated is selected one of the basal materials. It is preferable that a material having a maximum normalized attenuation coefficient in the first material group is selected as the first material. Also, a second material which is a material in a second material group which is a material group having a larger normalized attenuation coefficient than the normalized attenuation coefficients of the materials to be discriminated is selected as another one of the basal materials. It is preferable that a material having a minimum normalized attenuation coefficient is selected as the second material.

In FIG. 6, when water and an adipose tissue are the materials to be discriminated, one of graphite and polyethylene which are materials having smaller normalized attenuation coefficients, respectively, than those of the water and the adipose tissue, will be a candidate basal material. Also, any one of PTFE, aluminum, and calcium which are materials having larger normalized attenuation coefficients, respectively, than those of the water and the adipose tissue, will be a candidate basal material. Additionally, considering a degree of difference from the normalized attenuation coefficients of the water and the adipose tissue which are the materials to be discriminated and stability at ordinary temperature and pressure, a combination of polyethylene and PTFE may be selected as the basal materials.

Figure 7:
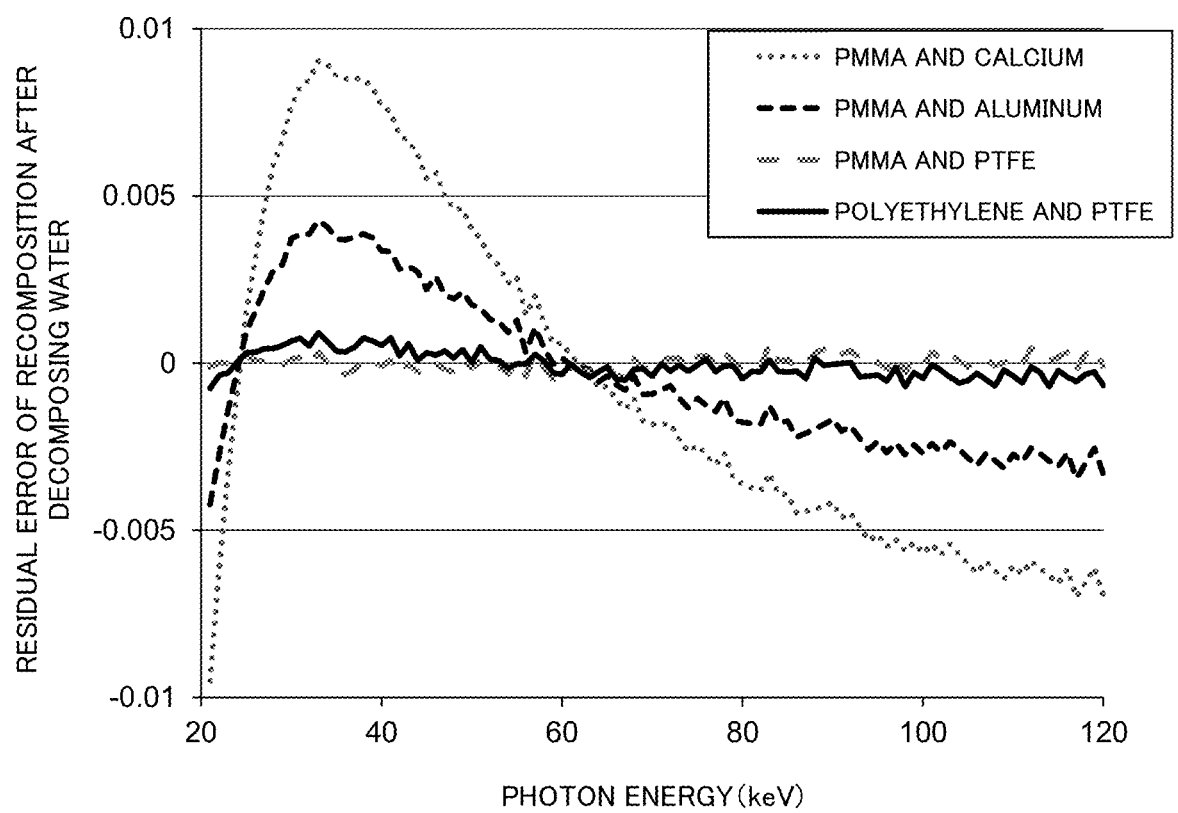
FIG. 7 is a diagram representing an example of relationships between a residual error of recomposition after decomposing water with multiple combinations of basal materials and photon energy.
Figure 8:
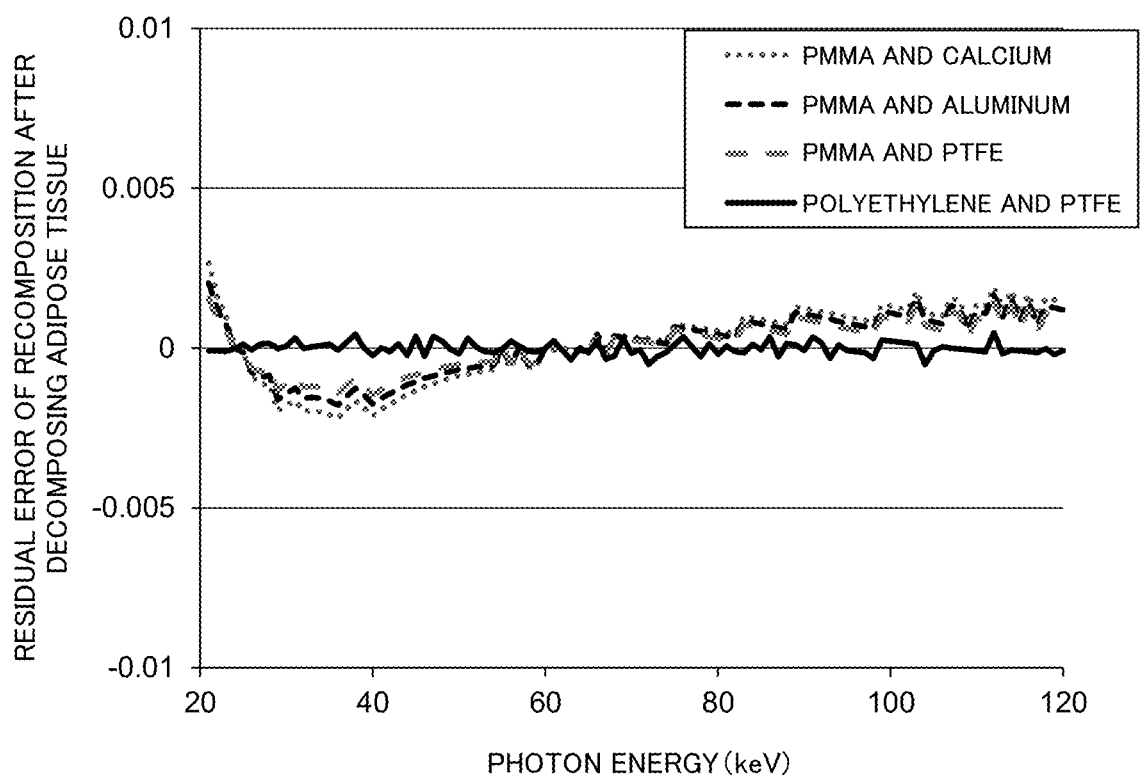
FIG. 8 is a diagram representing an example of relationships between a residual error of recomposition after decomposing an adipose tissue with multiple combinations of basal materials and photon energy.

How combinations of basal materials influence accuracy of material decomposition is described with FIGS. 7 and 8. After decomposing water with different combinations of basal materials, using basis coefficients obtained by the decomposition, linear attenuation coefficients are recomposed per unit of photon energy. FIG. 7 represents a result of subtracting linear attenuation coefficients of water from the recomposed linear attenuation coefficients. That is, the closer to zero a value on the ordinate over the entire range of photon energy, the higher will be material composition. When three combinations, each including PMMA, are compared, the accuracy of material decomposition increases in ascending order from calcium, aluminum, and to PTFE. Also, when two combinations, each including PTFE, are compared, PMMA contributes to higher accuracy than polyethylene, but both are less than 0.1%.

After decomposing an adipose tissue with different combinations of basal materials, using basis coefficients obtained by the decomposition, linear attenuation coefficients are recomposed. FIG. 8 represents a result of subtracting linear attenuation coefficients of the adipose tissue from the recomposed linear attenuation coefficients. When three combinations, each including PMMA, are compared, the accuracy of material decomposition increases in ascending order from calcium, aluminum, and to PTFE, as is the case for water. Also, when two combinations, each including PTFE, are compared, polyethylene contributes to higher accuracy than PMMA, and a combination of polyethylene and PTFE is less than 0.1%.

Returning to FIG. 6, when the normalized attenuation coefficients of the water and the adipose tissue are compared with the normalized attenuation coefficients of the combinations specified in FIGS. 7 and 8, PMMA and PTFE are closer to water, and polyethylene and PTFE are closer to the adipose tissue. That is, as the basal materials, by selecting materials having normalized attenuation coefficients with a smaller difference from the normalized attenuation coefficients of the materials to be discriminated, the accuracy of material decomposition can be increased.

(S404)

The computational device 108 calibrates the photon counting detectors using the basal materials selected at S403. More specifically, according to the configuration depicted in FIG. 2, among the combinations of the thicknesses of the basal materials, each time one combination is changed to another, a photon spectrum is measured. Additionally, if the materials to be discriminated are already determined, a range of the combinations of the thicknesses of the basal materials may be set restrictively.

Figure 9:
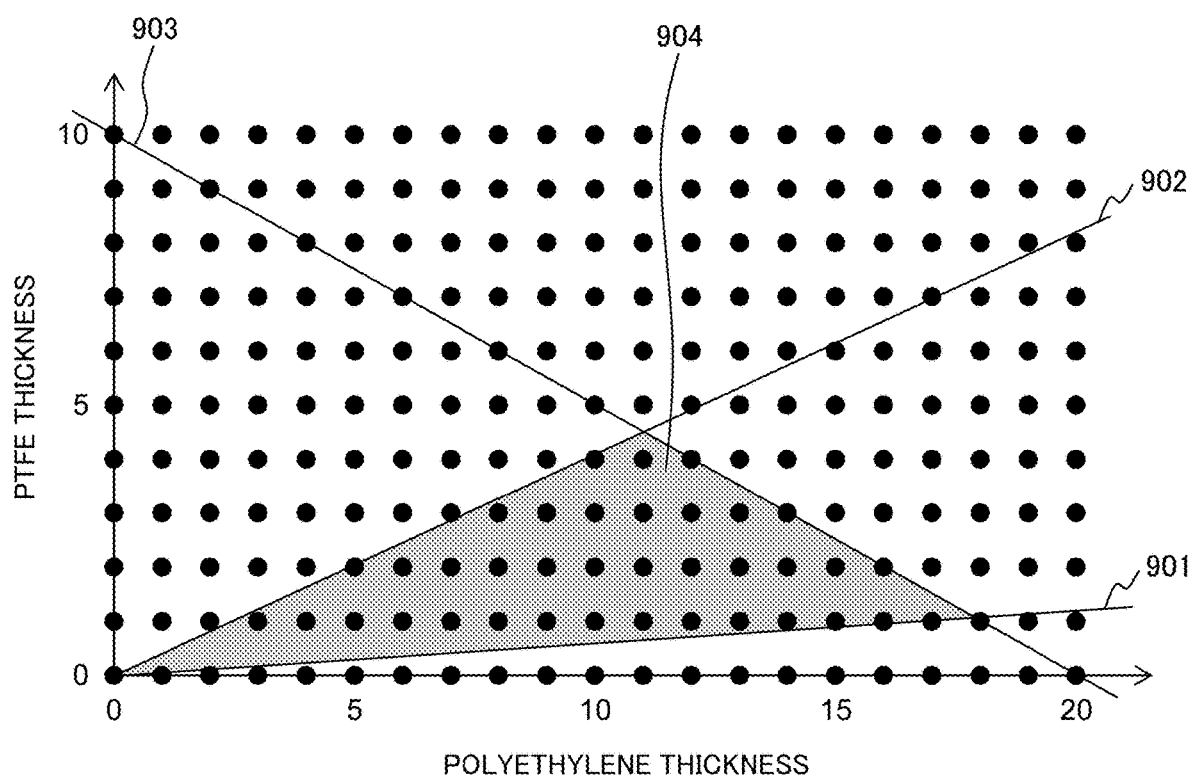
FIG. 9 is a diagram to explain setting a range of combinations of thicknesses of polyethylene and PTFE.

Setting a range of the combinations of the thicknesses of the basal materials is described with FIG. 9. In FIG. 9, the abscissa represents thickness of polyethylene which is one basal material, the ordinate represents thickness of PTFE which is the other basal material, and a full scale of both axes corresponds to a unit thickness of water. When water and an adipose tissue which are the materials to be discriminated are decomposed to polyethylene and PTFE, proportions of polyethylene thickness to the water and the adipose tissue are 60% and 88% respectively. Therefore, 2% is added to 88% and 90% is set as an upper limit 901 of the proportion of polyethylene. 5% is subtracted from 60% and 55% is set as a lower limit 902 of the proportion of polyethylene. Moreover, due to the fact that the sum of the proportion of polyethylene thickness and the proportion of PTFE thickness is 100% or less, an upper limit of combination 903 of polyethylene and PTFE is set. Then, a range surrounded by the upper limit 901 and the lower limit 902 of the proportion of polyethylene and the upper limit of combination 903 becomes a combination range 904 of polyethylene and PTFE.

Because a result of decomposition of a region where the water and the adipose tissue coexist which are the materials to be discriminated to polyethylene and PTFE falls within the combination range 904, the combinations of the thicknesses of polyethylene and PTFE which are used for calibration of the photon counting detectors may be restricted to the combination range 904. By restricting the combinations of the thicknesses of basal materials to a certain range, time and efforts required for calibration can be curbed.

Through the processing flow described hereinbefore, the photon counting detectors can be calibrated to enable discrimination between soft and adipose tissues with high accuracy. Also, by the X-ray CT apparatus 101 equipped with the thus calibrated photon counting detectors, it is possible to evaluate a difference in proportions of fat included in body tissues and therefore, this is useful in diagnostic imaging.

The foregoing has described an embodiment of both a radiation imaging apparatus and a calibration method for photon counting detectors of the present invention. The radiation imaging apparatus and the calibration method for photon counting detectors of the present invention are not limited to the foregoing embodiment, and it is possible to modify and embody components without departing from the scope of the invention. Also, multiple components disclosed in the foregoing embodiment may be combined, as appropriate. Furthermore, some components may be removed from all components set forth in the foregoing embodiment.

REFERENCE SIGNS LIST

101: X-ray CT apparatus, 102: gantry, 103: X-ray tube, 104: bow-tie filter, 105: bed, 106: subject, 107: detector panel, 108: computational device, 109: input device, 110: display device, 201: combination of basal materials, 301: storage unit, 302: calculation unit, 303: selection unit, 901: upper limit of proportion of polyethylene, 902: lower limit of proportion of polyethylene, 903: upper limit of combination, 904: combination range

What is claimed is:

1. A radiation imaging apparatus equipped with photon counting detectors which output an electric signal corresponding to photon energy which is energy of radiation photons incident thereon, the radiation imaging apparatus comprising:
    a storage unit which stores relationships between linear attenuation coefficients and the photon energy with regard to multiple materials;
    a calculation unit which calculates normalized attenuation coefficients which are linear attenuation coefficients normalized by dividing linear attenuation coefficients per unit of photon energy by a linear attenuation coefficient at given photon energy with respect to each material; and
    a selection unit which selects basal materials which are used in relation to materials to be discriminated which are intended to be discriminated, based on the normalized attenuation coefficients.

2. The radiation imaging apparatus according to claim 1, wherein the selection unit selects, as the basal materials, a first material which is a material in a first material group which is a material group having a smaller normalized attenuation coefficient than the normalized attenuation coefficients of the materials to be discriminated and a second material which is a material in a second material group which is a material group having a larger normalized attenuation coefficient than the normalized attenuation coefficients of the materials to be discriminated.

3. The radiation imaging apparatus according to claim 2, wherein the selection unit selects, as the first material, a material having a maximum normalized attenuation coefficient in the first material group and selects, as the second material, a material having a minimum normalized attenuation coefficient in the second material group.

4. The radiation imaging apparatus according to claim 2, wherein when water and an adipose tissue are included in the materials to be discriminated, the selection unit selects polyethylene and PTFE as the basal materials.

5. The radiation imaging apparatus according to claim 2, wherein the selection unit sets a range of combinations of thicknesses of the first material and the second material, based on proportions which are obtained by decomposing the materials to be discriminated with the first material and the second material.

6. The radiation imaging apparatus according to claim 1, wherein the selection unit selects materials having normalized attenuation coefficients with a smaller difference from the normalized attenuation coefficients of the materials to be discriminated as the basal materials.

7. The radiation imaging apparatus according to claim 1, wherein the given photon energy is maximum energy of the radiation photons.

8. A calibration method for photon counting detectors which output an electric signal corresponding to photon energy which is energy of radiation photons incident thereon, the calibration method comprising the steps of:
    obtaining relationships between linear attenuation coefficients and the photon energy with regard to multiple materials;
    calculating normalized attenuation coefficients which are linear attenuation coefficients normalized by dividing linear attenuation coefficients per unit of photon energy by a linear attenuation coefficient at given photon energy with respect to each material; and
    selecting basal materials which are used in relation to materials to be discriminated which are intended to be discriminated, based on the normalized attenuation coefficients.

* * * * *